United States Patent
Tanaka

[11] Patent Number: 5,612,754
[45] Date of Patent: Mar. 18, 1997

[54] EYE-REFRACTOMETER HAVING A FOGGING OPERATION

[75] Inventor: Takumi Tanaka, Hiratsuka, Japan

[73] Assignee: Nikon Corporation, Tokyo, Japan

[21] Appl. No.: 581,343

[22] Filed: Dec. 29, 1995

[30] Foreign Application Priority Data

Jan. 19, 1995 [JP] Japan ................................. 7-006538

[51] Int. Cl.$^6$ ........................................................ A61B 3/10
[52] U.S. Cl. ................................................ 351/211; 351/205
[58] Field of Search ................................. 351/211, 218, 351/221, 200, 205, 246, 212, 247

[56] References Cited

U.S. PATENT DOCUMENTS 5,555,039  9/1996  Iki et al. ................................ 351/205

*Primary Examiner*—Hung X. Dang
*Attorney, Agent, or Firm*—Shapiro and Shapiro

[57] ABSTRACT

An eye-refractometer includes a refracting power measurement system for objectively measuring the refracting power of an eye to be examined, a fogging mechanism for relaxing the accommodation of the eye to be examined by moving a target observed by the eye to be examined, a measurement switch for instructing measurement to start, a fogging operation suspension switch for instructing an operation of the fogging mechanism to be suspended, and a control system. When the measurement is instructed to start by the measurement switch and when the fogging operation is not instructed to be suspended by the fogging operation suspension switch, the control system operates the fogging mechanism, and thereafter, obtains data from the refracting power measurement system. When the measurement is instructed to start by the measurement switch and when the fogging operation is instructed to be suspended by the fogging operation suspension switch, the control system obtains data from the refracting power measurement system without operating the fogging mechanism.

6 Claims, 3 Drawing Sheets

5,612,754

EYE-REFRACTOMETER HAVING A FOGGING OPERATION

BACKGROUND OF THE INVENTION

1. Field of the Invention

The present invention relates to a hand-held eye-refractometer for objectively measuring the refracting power of an eye to be examined.

2. Related Background Art

Some eye-refractometers have a fogging function. Normally, when a target is presented to an eye to be examined, the function of the human eye called accommodation acts to fix itself on the target. For this reason, in order to measure an accurate refracting power, the accommodation function which acts to fix the eye on the target must be removed from the eye to be examined. In order to remove or relax the accommodation function that acts to fix the eye to be examined on the target, a fogging mechanism for moving the target is arranged.

In order to measure an accurate refracting power, the fogging operation for moving the target must be basically performed prior to obtention of the eye refracting power measurement data. For this reason, in a conventional eye-refractometer, a fogging operation is automatically started upon depression of a measurement switch, and thereafter, eye refracting power measurement data is obtained.

In the conventional eye-refractometer, upon depression of the measurement switch, a predetermined number of measurement data are obtained, and the plurality of data are subjected to statistical processing such as averaging processing. Thereafter, the statistical processing result is displayed.

The eye-refractometer is often used for eyes to be examined, which are impossible or hard to measure, i.e., the eyes of 0- to 3-year old babies, the eyes of patients under operation represented by that of cataract, the eyes of patients suffering from diseases such as nystagmus, the eyes of animals, and the like as objects to be measured. For most of these eyes to be examined, it is impossible or hard to expect fixation of gaze. Therefore, the operation of the fogging mechanism is often of no use, and the conventional eye-refractometer, which automatically starts a fogging operation upon depression of the measurement switch, vainly prolongs the measurement-time. Furthermore, as for the above-mentioned eyes to be examined, it is important for a measurement operator to obtain data. However, in the conventional eye-refractometer, a measurement operator can obtain a measurement value after the eye-refractometer itself obtains a predetermined number of data and performs statistical processing of these data. For example, when the eye-refractometer itself is hard to obtain a predetermined number of measurement data owing to the nature of a specific eye to be examined, a long period of time is required until a measurement value is obtained. In the worst case, the measurement operator cannot obtain a measurement value.

SUMMARY OF THE INVENTION

The present invention has been made in consideration of the conventional problems, and has its object to provide an eye-refractometer which can exclude unnecessary operations in accordance with situations, and can obtain a measurement value within a short time.

In order to achieve the above object, an eye-refractometer comprises:

a measurement switch used by a measurement operator to instruct measurement to start;

a fogging operation suspension switch used by the measurement operator to instruct an operation of a fogging mechanism to be suspended; and control means for, when the measurement is instructed to start by the measurement switch, operating the fogging mechanism unless the operation is instructed to be suspended by the fogging operation suspension switch, and thereafter, obtaining data from refracting power measurement means, and for, when the operation is instructed to be suspended by the fogging operation suspension switch even when the measurement is instructed to start by the measurement switch, obtaining data from the refracting power measurement means without operating the fogging mechanism.

The eye-refractometer may further comprise:

a data number changing switch used by the measurement operator to instruct the number of times of data obtention from the refracting power measurement means to be changed, and when the measurement is instructed to start by the measurement switch, the control means obtains a predetermined number of data from the refracting power measurement means and performs statistical processing of the plurality of data unless the number of times of data obtention is instructed to be changed by the data number changing switch, and when the number of times of data obtention is instructed to be changed by the data number changing switch, the control means obtains the changed number of data and performs the statistical processing of the plurality of data.

It is preferable that the eye-refractometer comprise state display means for allowing the measurement operator to visually recognize the operation state of the fogging mechanism.

According to the above object, another eye-refractometer comprises:

a measurement switch used by a measurement operator to instruct measurement to start;

a data number changing switch used by the measurement operator to instruct the number of times of data obtention from refracting power measurement means to be changed; and data obtention means for, when the measurement is instructed to start by the measurement switch, obtaining a predetermined number of data from the refracting power measurement means unless the number of times of data obtention is instructed to be changed by the data number changing switch, and for, when the measurement is instructed to start by the measurement switch and the number of times of data obtention is instructed to be changed by the data number changing switch, obtaining the changed number of data from the refracting power measurement means.

It is preferable that the other eye-refractometer that can achieve the above object comprise statistical processing means for performing statistical processing of the plurality of data obtained by the data obtention means. Furthermore, it is preferable that the eye-refractometer comprise state display means for allowing the measurement operator to visually recognize the change in the number of data to be obtained by the data obtention means.

When the measurement operator operates the measurement switch to instruct the measurement to start, the control means causes the fogging mechanism to operate unless the operation is instructed to be suspended by the fogging operation suspension switch, and thereafter, obtains data from the refracting power measurement means. On the other hand, when the measurement operator operates the measurement switch and the fogging operation suspension switch to instruct the measurement to start and the fogging operation to be suspended, the control means obtains data from the refracting power measurement means without operating the fogging mechanism. Therefore, in eyes to be examined, for which it is impossible or hard to expect fixation of gaze and for which the operation of the fogging mechanism is nonsense, data can be immediately obtained from the refracting power measurement means without operating the fogging mechanism, thus shortening the measurement time.

In the eye-refractometer having the data number changing switch, when the measurement is instructed to start by the measurement switch, the data obtention means obtains a predetermined number of data from the refracting power measurement means unless the number of times of data obtention is instructed to be changed by the data number changing switch. On the other hand, when the measurement is instructed to start by the measurement switch and the number of times of data obtention is instructed to be changed by the data number changing switch, the data obtention means obtains the changed number of data from the refracting power measurement means. As described above, since the number of data to be obtained from the refracting power measurement means can be changed, the measurement time can be shortened by decreasing the number of times of data obtention according to situations.

DETAILED DESCRIPTION OF THE PREFERRED EMBODIMENT

An embodiment of a hand-held eye-refractometer as an eye-refractometer according to the present invention will be described hereinafter with reference to FIGS. 1 to 4.

Figure 1:
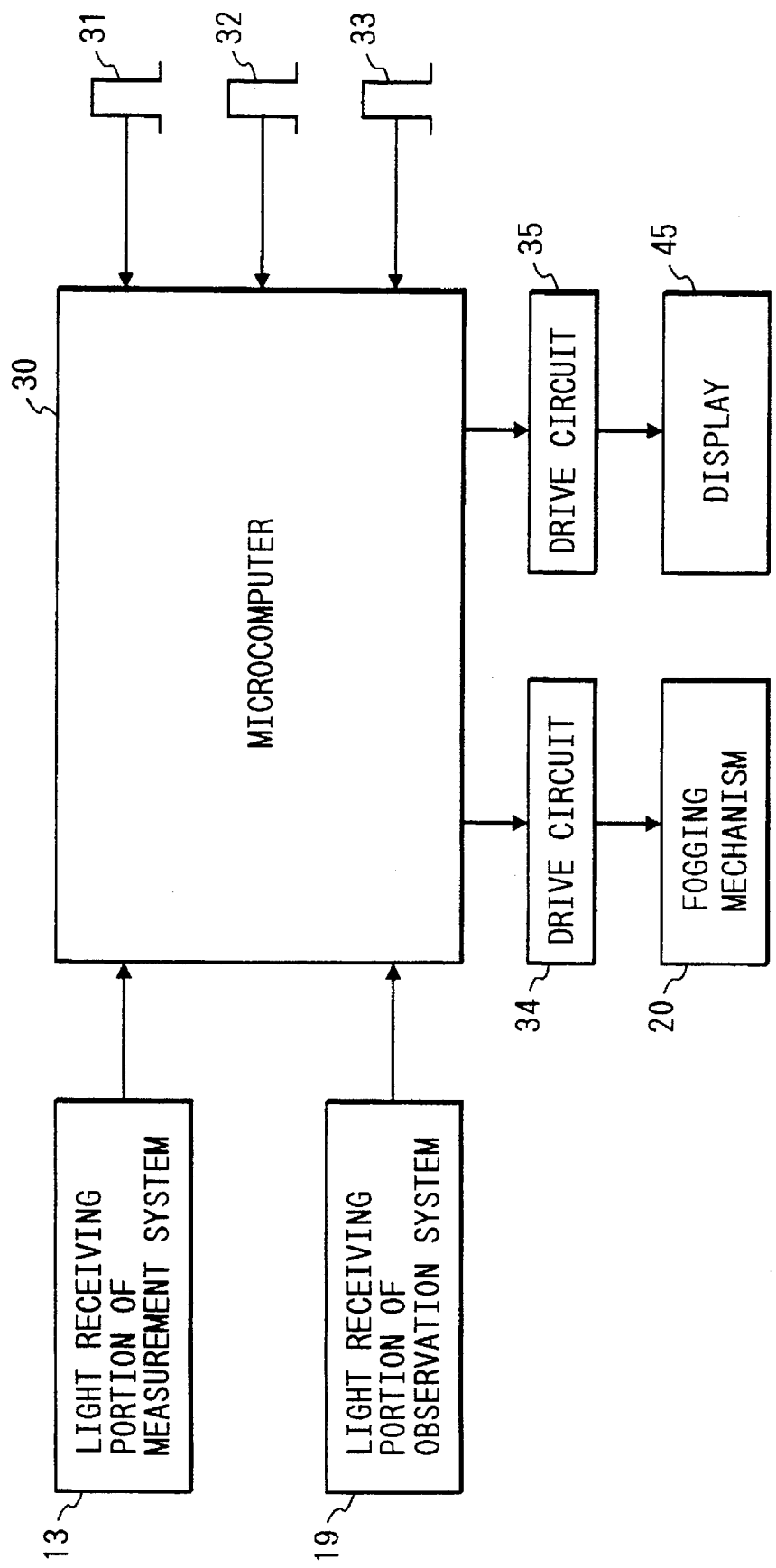
FIG. 1 is a block diagram of a hand-held eye-refractometer according to an embodiment of the present invention.
Figure 2:
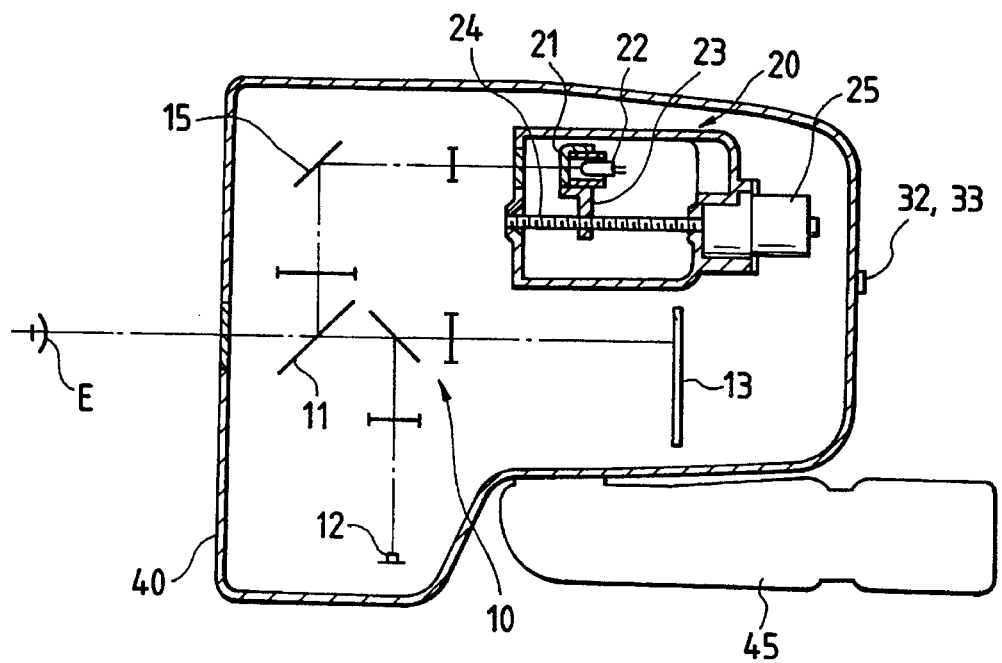
FIG. 2 is a cross-sectional view of the hand-held eye-refractometer according to the embodiment of the present invention.
Figure 3:
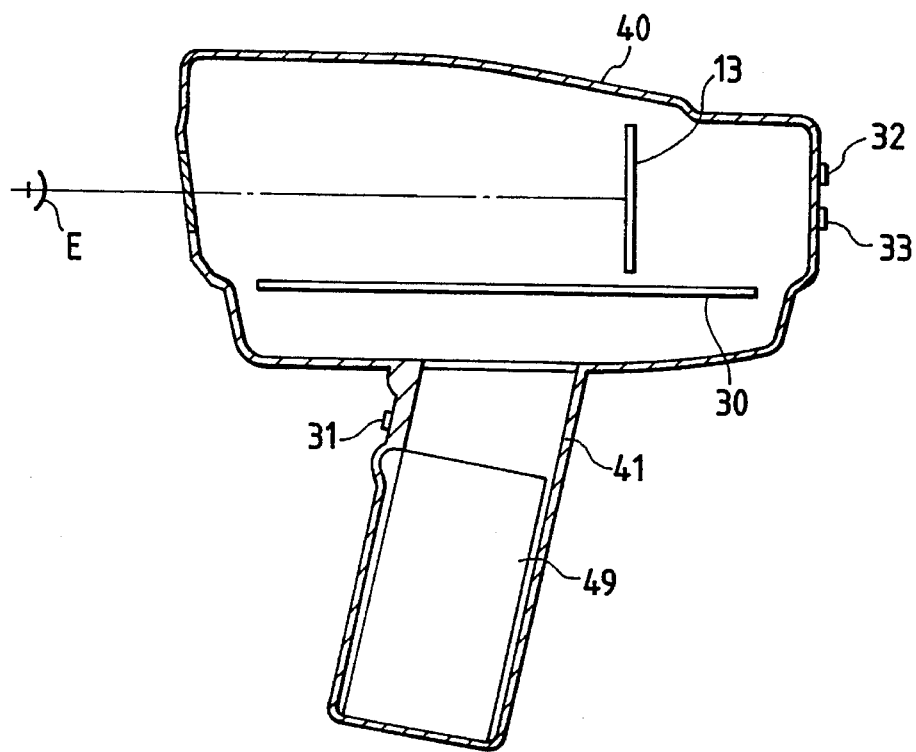
FIG. 3 is a longitudinal sectional view of the hand-held eye-refractometer according to the embodiment of the present invention.

As shown in FIGS. 2 and 3, the hand-held eye-refractometer of this embodiment comprises a refracting power measurement optical system 10, an observation optical system (not shown), a fogging optical system 15, a fogging mechanism 20 which has a target 21 and moves the target 21, various switches 31, 32, and 33, a microcomputer 30 for executing various arithmetic operations in response to operations of the switches 31, 32, and 33, a display 45 for displaying an image of an eye to be examined captured by the observation optical system, and displaying the operation results of the microcomputer 30, a battery 49 for operating the microcomputer 30, the fogging mechanism 20, the display 45, and the like, and a casing 40 for covering these components.

As shown in FIG. 3, a grip portion 41 to be gripped by a measurement operator is formed on the casing 40. The above-mentioned battery 49 is arranged in this grip portion 41.

The fogging mechanism 20 has the above-mentioned target 21, a target illumination source 22 for illuminating the target 21 with light from the rear side, a lead screw 24 which extends in a direction parallel to the optical axis of the fogging optical system 15, a motor 25 for rotating the lead screw 24, and a nut member 23 which supports the target 21 and the illumination source 22 and threadably engages with the lead screw 24.

The refracting power measurement optical system 10 has a light receiving portion 13 for receiving light reflected by an eye E to be examined, a half mirror 11 for guiding light reflected by the eye E to be examined to the light receiving portion 13, and guiding light from the fogging optical system 15 to the eye E to be examined, a light source 12 for illuminating the eye E to be examined with light, lenses, and the like. The observation optical system (not shown) has a light receiving portion 19 (shown in FIG. 1) for receiving light reflected by the eye E to be examined. Light reflected by the eye E to be examined is guided to the light receiving portion 13 of the refracting power measurement optical system 10 by the half mirror (not shown) constituting the refracting power measurement optical system 10, and is also guided to the light receiving portion 19 of the observation optical system.

The switches include the measurement switch 31 for instructing a measurement operation to start, the fogging operation suspension switch 32 for instructing the operation of the fogging mechanism 20 to be suspended, and the data number changing switch 33 for instructing the number of times of data obtention from the light receiving portion 13 of the measurement optical system to be changed. These switches 31, 32, and 33 are connected to the microcomputer 30 so as to input their operation signals to the microcomputer 30. The light receiving portion 13 of the measurement optical system is also connected to the microcomputer 30, so that an electrical signal obtained by converting light received by the light receiving portion 13, i.e., measurement data can be output to the microcomputer 30. The fogging mechanism 20 and the display 45 are connected to the microcomputer 30 via their drive circuits 34 and 35.

Figure 4:
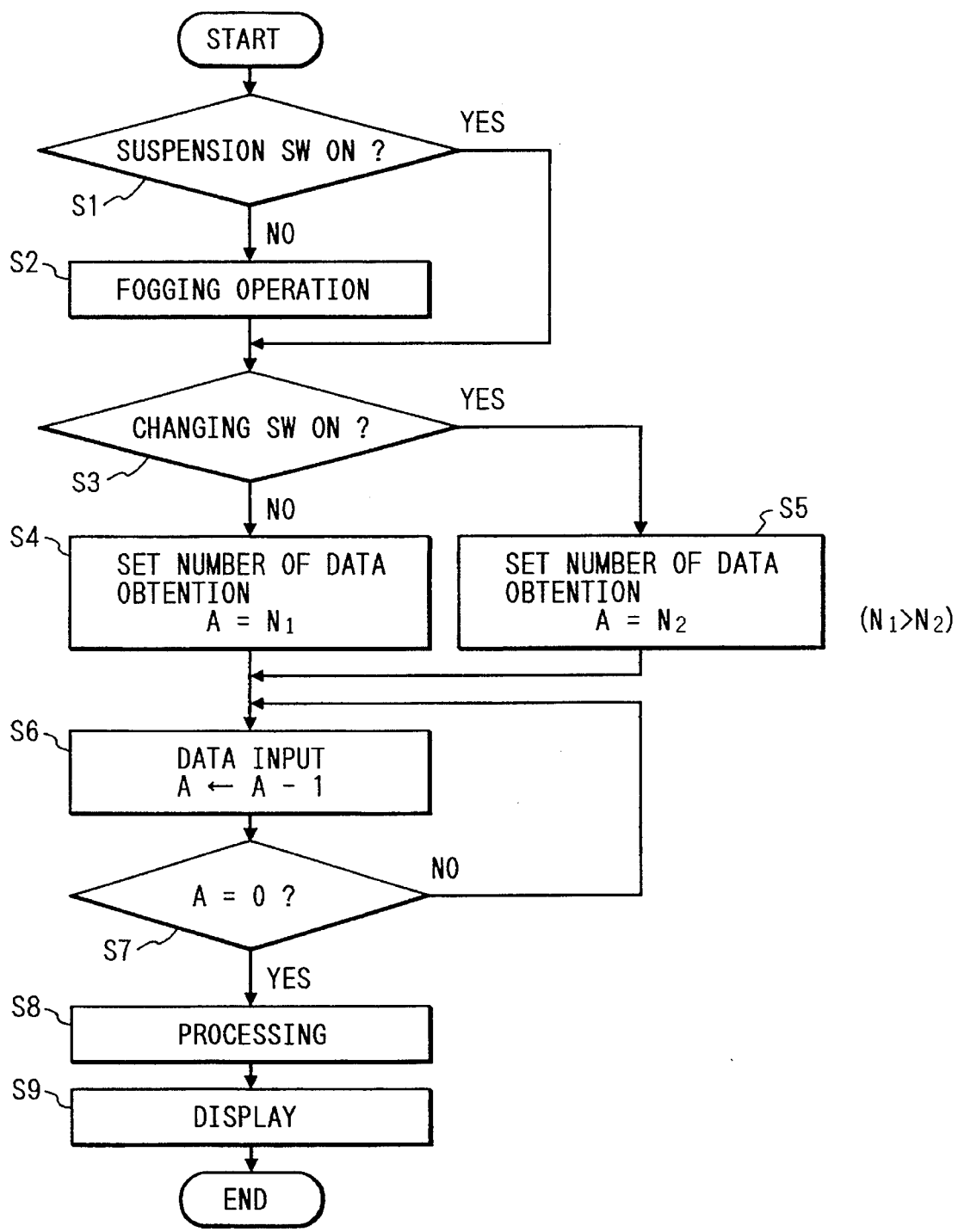
FIG. 4 is a flow chart showing the operation order of the hand-held eye-refractometer according to the embodiment of the present invention.

The microcomputer 30 has a signal processing unit (not shown) for converting an analog electrical signal from the light receiving portion 13 of the measurement optical system into a digital signal, a ROM (not shown) for storing a program for executing the flow shown in FIG. 4, various basic data, and the like, a CPU (not shown) for executing various arithmetic operations in accordance with the program stored in the ROM, a RAM (not shown) for temporarily storing the operation result of the CPU, and the like. In this embodiment, the control means, the data obtention means, and the statistical processing means are constituted by the microcomputer 30.

The operation of the hand-heldeye-refractometer according to this embodiment will be described below with reference to the flow chart shown in FIG. 4.

When the measurement operator depresses the measurement switch 31 to start the microcomputer 30 and the like, the microcomputer 30 checks if the fogging operation suspension switch 32 is depressed (step 1). If NO in step 1, the microcomputer 30 outputs a control signal to the fogging mechanism drive circuit 34 to operate the fogging mechanism 20 (step 2). In the operation of the fogging mechanism 20, the motor 25 is driven to rotate the lead screw 24 so as to move the target 21 and its illumination source 22, and the target illumination source 22 is turned on. The accommodation of the eye E to be examined, which is fixed on the target 21, is relaxed upon movement of the target 21.

If it is determined in step 1 that the fogging operation suspension switch 32 is depressed, the microcomputer 30 checks, without instructing execution of the fogging operation (step 2), whether or not the data number changing switch 33 is depressed (step 3). In this case, the display 45 displays "fogging operation suspended" in accordance with an instruction from the microcomputer 30. Upon completion of the fogging operation (step 2), the microcomputer 30 also checks whether or not the data number changing switch 33 is depressed. If NO in step 3, the microcomputer 30 sets the number of times of data obtention to a predetermined value $N_1$ (e.g., 16) (step 4); otherwise, the microcomputer 30 sets the number of times of data obtention to a value $N_2$ (e.g., 8) smaller than the value $N_1$ (step 5). Upon depression of the data number changing switch 33, the display 45 displays "number of obtained data decreased" in accordance with an instruction from the microcomputer 30.

Subsequently, the microcomputer 30 fetches data from the light receiving portion 13 of the measurement optical system, and repeats the data fetching operation until the number of fetched data reaches the number of obtained data set in step 4 or 5 (steps 6 and 7).

After a predetermined number of data are fetched, the microcomputer 30 performs statistical processing such as averaging processing of the plurality of fetched data (step 8), and displays the statistical processing result on the display 45 (step 9).

As described before under Related Background Art, the fogging operation is of no use for some eyes E to be examined, or it is preferable to complete the measurement within a short time at the cost of accuracy to some extent rather than obtaining an accurate measurement value by increasing the number of times of data obtention. In this embodiment, in such cases, when the fogging operation suspension switch 32 is depressed, the fogging operation is suspended; when the data number changing switch 33 is depressed, the number of obtained data is decreased, thus obtaining a measurement result within a short time. For this reason, when the hand-held eye-refractometer of this embodiment is used, the measurement can be performed even for a patient in hospital within a short time, thus reducing the burden on the patient. Furthermore, since the fogging operation can be skipped, the refracting power of the eye to be examined, for which it is impossible or hard to expect fixation of gaze, can be measured, thus broadening the range of patients that can be subjected to measurement.

In the above-mentioned embodiment, the fogging operation suspension switch for directly instructing the fogging operation to be suspended, and the data number changing switch for directly instructing the number of times of data obtention to be changed are arranged. In place of these switches, a high-speed switch for instructing the fogging operation to be suspended (substantially the same as the fogging operation suspension switch), and an ultra-high-speed switch for instructing the fogging operation to be suspended and the number of times of data obtention to be decreased may be arranged. In this manner, when the switches are arranged in correspondence with the degrees of shortening of the measurement time, it becomes easy to manage the measurement time. When the shortest measurement time is required, it can be realized by only one switch operation, i.e., one operation of the ultra-high-speed switch.

In the above-mentioned embodiment, in order to allow the measurement operator to recognize the operation states of the switches 32 and 33, in other words, the fogging operation state and the number of times of data obtention, the corresponding messages are displayed on the display 45. In place of these messages, LEDs, which are turned on upon depression of these switches, may be arranged.

According to the present invention, since the fogging operation suspension switch is arranged, if the fogging operation is not necessary, the fogging operation can be skipped by operating the suspension switch, thus shortening the measurement time. In the eye-refractometer with the data number changing switch as well, the number of data to be obtained can be decreased upon depression of this switch, thus shortening the measurement time.

Furthermore, according to the present invention, since the fogging operation can be skipped, the refracting powers of the eyes to be examined, for which it is impossible or hard to expect fixation of gaze, i.e., the eyes of 0- to 3-year old babies, the eyes of patients under operation represented by that of cataract, the eyes of patients suffering from diseases such as nystagmus, the eyes of animals, and the like, can be measured, thus broadening the range of patients that can be subjected to measurement.

What is claimed is:

1. An eye-refractometer comprising:

a refracting power measurement system for objectively measuring a refracting power of an eye to be examined;

a fogging mechanism for relaxing an accommodation power of the eye to be examined by moving a target observed by the eye to be examined;

a measurement switch for instructing measurement to start;

a fogging operation suspension switch for instructing an operation of said fogging mechanism to be suspended; and a control system for, when the measurement is instructed to start by said measurement switch and when the fogging operation is not instructed to be suspended by said fogging operation suspension switch, operating said fogging mechanism, and for obtaining, thereafter, data from said refracting power measurement system, and for, when the measurement is instructed to start by said measurement switch and when the fogging operation is instructed to be suspended by said fogging operation suspension switch, obtaining data from said refracting power measurement system without operating said fogging mechanism.

2. An eye-refractometer according to claim 1, further comprising: a data number changing switch for instructing the number of times of data obtention from said refracting power measurement system to be changed, wherein when the number of times of data obtention is not instructed to be changed by said data number changing switch, said control system obtains a predetermined number of data from said refracting power measurement system and performs statistical processing of the obtained data, and when the number of times of data obtention is instructed to be changed by said data number changing switch, said control system obtains the changed number of data and performs the statistical processing of the obtained data.

3. An eye-refractometer according to claim 1, further comprising: a display for allowing a measurement operator to visually recognize an operation state of-said fogging mechanism.

4. An eye-refractometer comprising:

a refracting power measurement system for objectively measuring a refracting power of an eye to be examined;

a measurement switch for instructing measurement to start;

a data number changing switch for instructing the number of time of data obtention from said refracting power measurement system to be changed; and data obtention device, when the measurement is instructed to start by said measurement switch and when the number of times of data obtention is not instructed to be changed by said data number changing switch, obtaining a predetermined number of data from said refracting power measurement system, and for, when the measurement is instructed to start by said measurement switch and when the number of times of data obtention is instructed to be changed by said data number changing switch, obtaining the changed number of data from said refracting power measurement system.

5. An eye-refractometer according to claim 4, further comprising: a statistical processor for performing statistical processing of a plurality of data obtained by said data obtention device.

6. An eye-refractometer according to claim 4, further comprising: a display for allowing a measurement operator to visually recognize the change of the number of data to be obtained by said data obtention device.

* * * * *